(12) United States Patent
Stork et al.

(10) Patent No.: US 6,620,773 B1
(45) Date of Patent: Sep. 16, 2003

(54) FOAMING OIL PREPARATION AND ITS USE

(75) Inventors: Anja Stork, Bonn (DE); Otto von Stetten, Aachen (DE)

(73) Assignee: Johnson & Johnson GmbH (DE)

( * ) Notice: Subject to any disclaimer, the term of this patent is extended or adjusted under 35 U.S.C. 154(b) by 0 days.

(21) Appl. No.: 09/762,177

(22) PCT Filed: Aug. 3, 1999

(86) PCT No.: PCT/EP99/05627

§ 371 (c)(1),
(2), (4) Date: Apr. 27, 2001

(87) PCT Pub. No.: WO00/07564

PCT Pub. Date: Feb. 17, 2000

(30) Foreign Application Priority Data

Aug. 4, 1998 (DE) .......................................... 198 35 239

(51) Int. Cl.⁷ .............................. C11D 3/36; C11D 3/382
(52) U.S. Cl. ........................ 510/130; 510/119; 510/122; 510/123; 510/127; 510/130; 510/135; 510/136; 510/242; 510/417; 510/432; 510/466; 510/490; 510/125; 510/407; 510/413; 510/414; 510/424; 510/431; 510/436
(58) Field of Search ................................ 510/119, 122, 510/123, 127, 130, 135, 136, 242, 417, 432, 466, 490, 125, 407, 413, 414, 424, 431, 436

(56) References Cited

U.S. PATENT DOCUMENTS

| | | | |
|---|---|---|---|
| 4,144,201 A | | 3/1979 | Winterbotham et al. ..... 252/547 |
| 4,536,519 A | * | 8/1985 | Suzuki et al. ................ 514/785 |
| 4,939,179 A | * | 7/1990 | Cheney et al. ............... 514/789 |
| 4,963,535 A | | 10/1990 | Sebag et al. ................... 514/54 |
| 5,334,325 A | | 8/1994 | Chaussee |
| 5,776,872 A | * | 7/1998 | Giret et al. .................. 510/124 |
| 6,004,915 A | * | 12/1999 | Elliott et al. ................. 510/135 |
| 6,333,362 B1 | * | 12/2001 | Lorant ......................... 516/8.1 |

FOREIGN PATENT DOCUMENTS

| | | |
|---|---|---|
| DE | 19501185 A1 | 7/1996 |
| EP | 0312962 A2 | 4/1989 |
| GB | 2139112 A | 11/1984 |
| GB | 2 283 755 A | 5/1995 |
| WO | WO 94/17783 | 8/1994 |
| WO | 98/00495 A1 | 1/1998 |
| WO | 98/27936 A1 | 7/1998 |
| WO | 98/27937 A1 | 7/1998 |

\* cited by examiner

*Primary Examiner*—Charles Boyer
(74) *Attorney, Agent, or Firm*—Erin M. Harriman

(57) ABSTRACT

The present invention relates to a composition which comprises at least a surfactant mixture and an oil component, the surfactant mixture comprising at least an anionic or zwitterionic surfactant, a nonionic surfactant and an alkyl phosphate component. The composition according to the invention is extremely well tolerated by the skin, mucosa and eyes, and has excellent foam formation.

37 Claims, No Drawings

FOAMING OIL PREPARATION AND ITS USE

DESCRIPTION

The invention relates to a composition which comprises at least a surfactant and an oil component, and to its uses.

Cleansing the skin results, irrespective of the surfactants added, in swelling of the horny layers, water-soluble constituents of dirt being washed off and substances endogenous to the skin being washed out. In the process, naturally occurring skin fats are also dissolved and removed, making it necessary to replenish the skin with these or subsidiary protective factors.

For this purpose, oil preparations are used as bath or shower preparations in the art. These should be provided as single-phase systems which, on contact with water, forms an emulsion or a full solubilizate in preference to dividing into two phases and, for example, the oil phase separating out on the surface of the water. As a result of the formation of an emulsion, the skin, and very particularly dry skin, is, during the cleansing operation, better cared for with the preferred oils than in two-phase systems.

Oil preparations with and without surfactants are known in the art.

Surfactant-containing oil preparations for use as cosmetic or dermatological shower oils are described in DE 44 24 210 C2. The oil preparations have a content of at most 55% of surfactants and also at least 45% of a selection of oil components. In other respects, the oil preparation described therein is anhydrous. The surfactants are chosen from the group of fatty alcohol ethoxylates, fatty alcohol sulphates, amides of fatty alcohol sulphates, fatty alcohol ether sulphates, amides of fatty alcohol ether sulphates, fatty acid monoethanolamides and fatty acid diethanolamides. Although no limitations are made on the choice of oil components, although triglycerides are mentioned as being particularly preferred in this publication, the person skilled in the art knows, and this is also shown by the examples given in the said publication, that for the surfactant-containing preparations customary to date, either a paraffin oil or castor oil content is obligatory, particularly when the oil component of the oil preparation is entirely vegetable in origin.

When formulating an oil preparation, particular care should be taken when it is used by people who suffer from atopic eczema and also those people whose skin requires special care, thus, for example, as a result of damage caused by the environment, irritation, light damage and ageing skin.

The object of the present invention is to provide a composition which foams well and is tolerated particularly well by the skin, mucosa and eyes, without a limitation in the choice of oil components being necessary. It is also the object of the present invention to keep the content of surfactants as low as possible.

According to the invention, the object is achieved by a composition comprising at least a surfactant mixture and an oil component, the surfactant mixture comprising at least
   an anionic or zwitterionic surfactant,
   a nonionic surfactant and
   an alkyl phosphate component.

Furthermore, the invention proposes that, based on the total weight of the composition, the proportion of the surfactant is from 15 to 50% and that of the oil component is from 50 to 85%.

The composition according to the invention can, furthermore, be essentially water-free and/or comprise at least one further component chosen from the group consisting of cosmetic and/or pharmaceutical auxiliaries, additives and active ingredients.

In an embodiment of the composition according to the invention, the content of anionic and/or zwitterionic surfactant, based on the total weight, is from 0.1 to 30%.

In a preferred embodiment, the content of anionic and/or zwitterionic surfactant is from 3 to 20%.

In a particularly preferred embodiment, the content of anionic and/or zwitterionic surfactant is from 5 to 15%.

In an embodiment of the composition according to the invention, the anionic and/or zwitterionic surfactant is chosen from the group consisting of alkyl alcohol sulphates, ethoxylated alkyl alcohol sulphates and alkyl-midopropylbetaine.

In a preferred embodiment, the alcohol sulphates and/or the ethoxylated alkyl alcohol sulphates have the following structure:

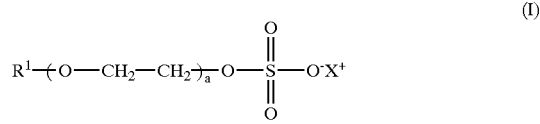

(I)

where a is an integer from 0 to 10, $R^1$ is an unbranched or branched, saturated or unsaturated alkyl group having from 8 to 24 carbon atoms and $X^+$ is chosen from the group consisting of alkali metal ions, alkaline earth metal ions and ammonium ions, the ammonium ions being substituted by $\geq 0$ alkyl groups and/or $\geq 0$ hydroxyalkyl groups, and the alkyl and/or hydroxyalkyl groups being branched or unbranched, saturated or unsaturated.

In a further preferred embodiment, a is an integer between 1 and 6.

In one embodiment, furthermore, the alkyl and/or hydroxy-alkyl group(s) has/have a chain length of from 1 to 8 carbon atoms.

In the composition according to the invention, the content of nonionic surfactant, based on the total weight is of the composition, is from 1 to 28%.

In a preferred embodiment, the content of nonionic surfactant is from 5 to 25%.

In a particularly preferred embodiment, the content of nonionic surfactant is from 7 to 23%.

In a further embodiment of the composition according to the invention, the nonionic surfactant is chosen from the group consisting of fatty alcohol ethoxylates, amides of alkyl fatty acids, ethoxylated fatty acid amides and polyoxyethylene-polyoxypropylene block polymers.

In a preferred embodiment, the nonionic surfactant is a fatty alcohol ethoxylate.

In a particularly preferred embodiment, the fatty alcohol ethoxylates have the following structure:

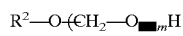

where $R^2$ is chosen from the group consisting of branched and unbranched, saturated and unsaturated alkyl groups having from 8 to 24 carbon atoms and m is an integer between 1 and 40.

In a further embodiment of the composition according to the invention, the fatty acid amides have the following structure:

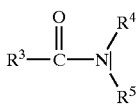 (IIIa)

and/or the ethoxylated fatty acid amides have the following structures (IIb) and/or (IIIc)

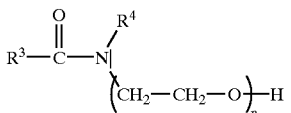 (IIIb)

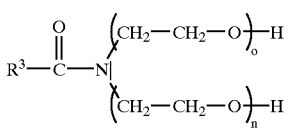 (IIIc)

where $R^3$ is chosen from the group consisting of branched and unbranched, saturated and unsaturated alkyl groups having from 8 to 24 carbon atoms, and n and o are in each case and independently of one another an integer between 0 and 8, $R^4$ and $R^5$ are in each case and independently of one another H, an alkyl group or a hydroxyalkyl group.

In the composition according to the invention, the polyoxyethylene-polyoxypropylene block polymers have from 4 to 40 ethylene oxide groups per molecule and/or from 10 to 50 propylene oxide groups per molecule.

In a further embodiment of the composition according to the invention, the content, based on the total weight of the composition, of the alkyl phosphate component is from 0.5 to 25%.

In a preferred embodiment, the content of the alkyl phosphate component is from 1.5 to 20%.

In a particularly preferred embodiment, the content of the alkyl phosphate component is from 1.8 to 18%.

In an embodiment of the composition according to the invention, the alkyl phosphate component has at least one of the following structures:

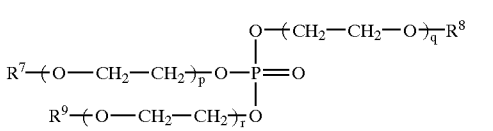 (IVa)

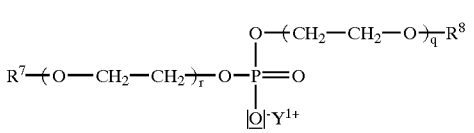 (IVb)

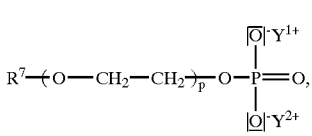 (IVc)

where $R^7$ is chosen from the group consisting of unbranched and branched, saturated and unsaturated alkyl groups having from 8 to 24 carbon atoms;

$R^8$ and $R^9$ are in each case and independently of one another chosen from the group consisting of H and unbranched and branched, saturated and unsaturated alkyl groups having from 8 to 24 carbon atoms;

$Y^1$ and $Y^2$ are in each case and independently of one another chosen from the group consisting of alkali metal ions, alkaline earth metal ions and ammonium ions, the nitrogen atom of the ammonium ion being substituted by $\geq 0$ alkyl groups and/or $\geq 0$ hydroxyalkyl groups; and p, q and r are in each case and independently of one another an integer between 0 and 10.

In the compositions according to the invention, $R^4$, $R^5$ and the substituents on the N atom in $Y^1$ and $Y^2$ are in each case and independently of one another chosen from the group consisting of alkyl and/or hydroxyalkyl groups which are unbranched or branched, saturated or unsaturated and/or have a chain length of from 1 to 8 carbon atoms.

In a particularly preferred embodiment, the alkyl phosphate component can be a mixture of two or more of the abovementioned alkyl phosphates and/or their salts.

In the composition according to the invention, the oil component is chosen from the group consisting of natural oils having a high content of triglycerides, modified oils which comprise mixtures of mono- and diglycerides, paraffin oil, ester oils and silicone oils.

Furthermore, the glycerides comprise fatty acids chosen from the group consisting of branched, unbranched, saturated and unsaturated fatty acids. In this connection, particular preference is given to fatty acids having from 8 to 24 carbon atoms.

In a preferred embodiment of the composition according to the invention, the oil component comprising a natural oil has a high content of polyunsaturated fatty acids, the linoleic acid to c-linolenic acid ratio being between 15:1 and 5:1.

In this connection, the ratio is particularly preferably between 13:1 and 7:1.

Very particular preference is given to a composition in which the ratio is between 11:1 and 9:1.

Furthermore, the invention proposes that in an embodiment of the composition according to the invention, the oil component is chosen from the group consisting of paraffin oil, modified coconut oil, soybean oil, sunflower oil, wheatgerm oil, linseed oil, thistle oil and grapeseed oil.

In a preferred embodiment, the modified coconut oil has a cloud point of <5° C.

In a further preferred embodiment of the composition according to the invention, in each case based on the total weight of the formulation, the surfactant component constitutes from 15 to 35% by weight, in which case the surfactant component comprises from 5 to 15% of TIPA laureth sulphate, from 10 to 25% of laureth-3 and from 1.5 to 15% of potassium deceth-4 phosphate, and the oil component comprises from 5 to 55% of soybean oil, from 0 to 25% of sunflower oil and from 0 to 30% of paraffin oil.

In accordance with the invention, the composition according to the invention can be used to prepare a foaming oil preparation.

Furthermore, the invention proposes using the composition according to the invention for cosmetic and/or pharmaceutical purposes.

The composition according to the invention can be used as an oil bath, shower preparation, face-cleansing fluid, make-up remover or body wash.

Furthermore, the composition according to the invention can be used for the treatment of dry skin conditions and atopic eczema, particular preference being given to use of the composition according to the invention in the therapy-free interval.

The present invention is based on the surprising finding that in the case of a composition which has at least a surfactant mixture and an oil component, a clear, single-phase and, in particular, foaming oil preparation is possible if the surfactant mixture comprises at least an anionic or zwitterionic surfactant, a nonionic surfactant and an alkyl phosphate component. The composition according to the invention is also advantageous insofar as no limitations at all are required on the choice of oil component. Accordingly, it is possible to formulate products whose oil component is of a purely vegetable origin without the composition having to contain castor oil.

Moreover, the composition according to the invention is particularly well tolerated by the skin, mucosa and eyes and as a result of their particular mildness during or after the cleansing process, hardly impair the natural lipid layer of the skin. This surprising effect is also used as a basis for the use of the composition according to the invention for cosmetic and pharmaceutical purposes, thus also for the treatment of dry skin conditions and atopic eczema, the latter in particular during the so-called therapy-free interval. In this connection, therapy-free interval is taken to mean that period during which the medicaments used in the treatment of atopic eczema, in particular those used during or directly after an acute attack, which normally contain cortisone, are or have been stopped as a result of the acute attack subsiding.

The use of the preparation according to the invention as a bath or shower preparation and also as a face-cleansing fluid, make-up remover or body wash is associated with excellent tolerability and a significant improvement in the condition of the skin, as has been determined in test series. Measurements after a single application demonstrate a long-lasting effect, for example the improvement in the skin moisture over 24 hours.

The tolerability by the eyes has likewise been tested, and for the examples listed herein, it has been shown that despite a surfactant content of about 30%, a preparation of the composition according to the invention did not, surprisingly, lead to a burning in the eyes.

With regard to the terminology chosen herein, it is recognized that the alkyl phosphate component can adopt either the character of a nonionic or else an anionic/zwitterionic surfactant, depending on its various possible modifications. The present invention should, however, be taken to mean that in such cases in the composition according to the invention, at least one different nonionic surfactant and one likewise different anionic or zwitterionic surfactant should also be used in each case in addition to the respective alkyl phosphate component.

In the surfactants described herein, the radicals $R^1$, $R^2$, $R^3$, $R^7$, $R^8$ and $R^9$ are inter alia chosen from the group consisting of H, unbranched and branched, saturated and unsaturated alkyl groups having from 8 to 24 carbon atoms. This also includes combinations of these types of alkyl groups, i.e. unbranched saturated alkyl groups, unbranched unsaturated alkyl groups, branched saturated alkyl groups and branched unsaturated alkyl groups, where the carbon backbone making up the carbon atoms preferably has from 8 to 24 carbon atoms.

The alkyl groups of the surfactants can thus also have the alkyl radicals of palmitic, stearic, isostearic, hydroxystearic, ricinoleic, oleic, behenic, arachidonic and elaidic acid. Equally, they may contain those alkyl radicals which are present in the coconut fraction (C8 to C22; containing principally branched alkyl radicals and linoleic and linolenic acid), palm fraction or tallow fraction. Furthermore, the alkyl groups of the surfactants may contain alkyl groups of C12 to C15 fatty alcohols (including oxo alcohols and branched alcohols).

Further, in connection with the present invention, the alkyl and hydroxyalkyl groups which are present herein as substituents for ammonium ions or bonded to the amide nitrogen, should be able to be chosen from the group consisting of branched and unbranched, saturated and unsaturated alkyl groups having, preferably, from 1 to 8 carbon atoms, it being possible for the alkyl groups here also to be those which are branched-saturated, branched-unsaturated, unbranched-saturated or unbranched-unsaturated.

In a nonlimiting manner, such alkyl groups include, in particular, methyl, ethyl, propyl, butyl, isopropyl, isobutyl, amyl, hexvl, isoamyl, octyl, ethanol, propanol, isopropanol, butanol, diisopropanol, isobutanol and the like.

With this type of alkyl or hydroxyalkyl groups, very particular preference is given to hydroxyalkyl-substituted ammonium ions, such as, for example, triisopropanolammonium, triethanolammonium, monoisopropanolammonium or monoethanolammonium ions.

In principle, it is applicable that the definition of alkyl as a general designation for monovalent alkane radicals is not used herein with the astringency according to the definition, as can be seen from the above, that unsaturated alkyl groups and those with OH groups are also used.

At least some of the surfactants used herein are commercially available. For example, fatty alcohol sulphates are marketed by Zschimmer & Schwarz under the name "Zetesol TP 200". "Zetesol TP 200" is a mixture of TIPA laureth sulphate and propylene glycol in a ratio of 94% to 6%. TIPA laureth sulphate is, according to INCI, to which reference is made herein, the name for triisopropylammonium lauryl PEG sulphate.

One example of the commercial availability of the alkyl phosphates mentioned herein is "Phosphetal 201 K", which is also a commercial product from Zschimmer & Schwartz and is a mixture of mono- and disubstituted phosphoric acid. The alkyl alcohol component is in this case decyl PEG-4; said phosphates are in the form of the potassium salt. The name of these alkyl phosphates according to INCI nomenclature is: potassium deceth-4 phosphate.

As regards the alkyl phosphate, it should again be pointed out at this point that these can also be in the form of ethoxylated alkyl phosphates for the purposes of the invention, it being possible for the degree of ethoxylation typically to be between 1 and 10. The alkyl phosphates can in the widest sense be in the form of mono-, di- or trialkyl phosphates or as salts thereof, irrespective of the degree of ethoxylation.

In connection with the present composition according to the invention, the oil component can be chosen without any limitation. The alkyl radicals in the oils can also correspond to those which are present in the coconut fraction (C8 to C22; predominantly unbranched, comprising linoleic and linolenic acid), palmitic, stearic, isostearic, hydroxystearic, ricinoleic, oleic, behenic, arachidonic and elaidic acid.

Modified coconut oil is available under the trade name "Myritol 331" from Henkel KGaA and is a mixture of mono-, di- and triglycerides which are derived from coconut oil.

The silicone oils suitable for use for the composition according to the invention include, in particular, those which are described in the sections on dimethicones and cyclomethicones in the "International Cosmetic Ingredient Dictionary and Handbook", 7th Edition, 1997; Ed: The Cosmetic Toiletry and Fragrance Association, Washington D.C., USA, and which are incorporated herein by reference.

The ester oils suitable for use for the composition according to the invention include the ester oils known to skilled persons in the field of cosmetics.

The percentages given herein are percentages by weight and refer to the total weight of the respective formulation.

The ratio of linoleic to α-linolenic acid is a weight ratio.

The above invention is illustrated by reference to the following examples, although these are not intended to be limiting.

The compounds mentioned herein correspond to INCI nomenclature. INCI means "International Nomenclature of Cosmetic Ingredients" and is known to experts in the field of cosmetics. This nomenclature is laid down in the "International Cosmetic Ingredient Dictionary and Handbook", 7th Edition, 1997; Ed.: The Cosmetic Toiletry and Fragrance Association, Washington, D.C., USA, whose disclosure in this respect is incorporated herein by reference.

The oil preparations below were prepared by mixing together the individual components in a stainless steel container.

EXAMPLE 1

Foaming Oil Preparation Consisting of (In Percentages by Weight)

| | |
|---|---|
| TIPA laureth sulphate, propylene glycol | 9.30% |
| Laureth-3 | 15.90% |
| Potassium deceth-4 phosphate | 3.00% |
| Paraffin oil | 23.30% |
| Soybean oil | 35.40% |
| Sunflower oil | 12.60% |
| Perfume | 0.50% |

EXAMPLE 2

Foaming Oil Preparation Consisting of (In Percentages by Weight)

| | |
|---|---|
| TIPA laureth sulphate, propylene glycol | 7.40% |
| Laureth-3 | 15.80% |
| Potassium deceth-4 phosphate | 3.00% |
| Cocamide-DEA | 3.00% |
| Paraffin oil | 22.30% |
| Soybean oil | 35.40% |
| Sunflower oil | 12.60% |
| Perfume | 0.50% |

EXAMPLE 3

Foaming Oil Preparation Consisting of (In Percentages by Weight)

| | |
|---|---|
| TIPA laureth sulphate, propylene glycol | 12.20% |
| Laureth-3 | 20.90% |
| Potassium deceth-4 phosphate | 3.90% |
| Soybean oil | 35.40% |
| Sunflower oil | 27.60% |

EXAMPLE 4

Foaming Oil Preparation Consisting of (In Percentages by Weight)

| | |
|---|---|
| TIPA laureth sulphate, propylene glycol | 6.30% |
| Laureth-3 | 10.70% |
| Potassium deceth-4 phosphate | 2.00% |
| Paraffin oil | 61.00% |
| Modified coconut oil | 20.00% |

EXAMPLE 5

Foaming Oil Preparation Consisting of (In Percentages by Weight)

| | |
|---|---|
| TIPA laureth sulphate, propylene glycol | 7.30% |
| Laureth-3 | 13.60% |
| Potassium deceth-4 phosphate | 2.60% |
| Paraffin oil | 25.10% |
| Soybean oil | 37.60% |
| Sunflower oil | 13.30% |
| Perfume | 0.50% |

EXAMPLE 6

Foaming Oil Treparation Consisting of (In Percentages by Weight)

| | |
|---|---|
| TIPA laureth sulphate, propylene glycol | 8.30% |
| Laureth-3 | 14.10% |
| Potassium deceth-4 phosphate | 2.70% |
| Soybean oil | 42.80% |
| Sunflower oil | 9.80 |
| Modified coconut oil | 15.00% |
| Wheatgerm oil | 7.50 |

EXAMPLE 7

Foaming Oil Preparation Consisting of (In Percentages by Weight)

| | |
|---|---|
| TIPA laureth sulphate, propylene glycol | 11.60% |
| Laureth-3 | 19.80% |
| Potassium deceth-4 phosphate | 3.70% |
| Modified coconut oil | 15.00% |
| Wheatgerm oil | 50.00% |

The features of the invention disclosed in the above description, including the examples, and the claims may be significant, either individually or in any combination, for realizing the invention in its various embodiments.

What is claimed is:

1. A foaming oil composition comprising at least a surfactant mixture and an oil component, characterized in that the surfactant mixture comprises (a) an anionic or zwitterionic surfactant; (b) a nonionic surfactant and (c) at least one ethoxylated alkyl phosphate ester component; wherein said ethoxylated alkyl phosphate ester is selected from one of the following structures:

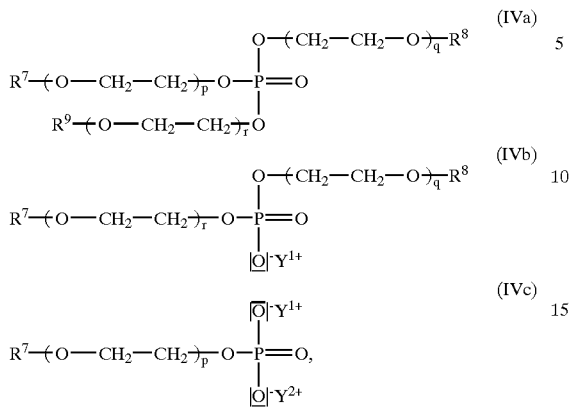

where $R^7$ is chosen from the group consisting of unbranched and branched, saturated and unsaturated alkyl groups having from 8 to 24 carbon atoms;

$R^8$ and $R^9$ are in each case and independently of one another chosen from the alkyl group consisting of H and unbranched and branched, saturated and unsaturated groups having from 8 to 24 carbon atoms;

$Y^1$ and $Y^2$ are in each case and independently of one another chosen from the group consisting of alkali metal ions, alkaline earth metal ions and ammonium ions, the nitrogen atom of the ammonium ion being substituted by $\geq 0$ groups and/or $\geq 0$ hydroxyalkyl groups; and p, q, and r are in each case and independently of one another an integer between 0 and 10, wherein the composition comprises at least one ethoxylated phosphate ester of the above formula wherein at least one of p, q and r is an integer between 1 and 10; wherein said composition comprises at least one anionic or zwitterionic surfactant which is different from said at least one ethoxylated alkyl phosphate and at least one non-ionic surfactant which is different from said at least one ethoxylated alkyl phosphate.

2. A composition according to claim 1, characterized in that, based on the total weight of the composition, the proportion of the surfactant mixture ranges from about 15% to about 50% and that of the oil component ranges from about 50% to about 85%.

3. A composition according to claim 1, characterized in that the composition is essentially water-free and/or comprises at least one further component chosen from the group consisting of cosmetic and/or pharmaceutical auxiliaries, additives and active ingredients.

4. A composition according to claim 1 characterized in that the content of anionic and/or zwitterionic surfactant, based on the total weight of the composition, ranges from about 0.1% to about 30%.

5. A composition according to claim 1 characterized in that the content of anionic and/or zwitterionic surfactant, based on the total weight of the composition, ranges from about 3% to about 20%.

6. A composition according to claim 1 characterized in that the content of anionic and/or zwitterionic surfactant, based on the total weight of the composition, ranges from about 5% to about 15%.

7. A composition according to claim 1 characterized in that the anionic and/or zwitterinic surfactant is chosen from the group consisting of alkyl alcohol sulphates, ethoxylated alkyl alcohol sulphates and alkylamidopropylbetaine.

8. Composition according to claim 7, characterized in that the alkyl alcohol sulphates and/or the ethoxylated alkyl alcohol sulphates have the following structure:

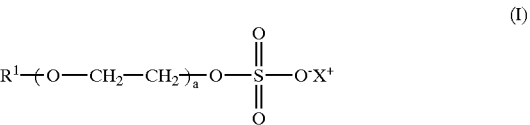

where a is an integer from 0 to 10, $R^1$ is an unbranched or branched, saturated or unsaturated alkyl group having from 8 to 24 carbon atoms and $X^+$ is chosen from the group consisting of alkali metal ions, alkaline earth metal ions and ammonium ions, the ammonium ions being substituted by $\geq 0$ alkyl groups and/or $\geq 0$ hydroxyalkyl groups, and the alkyl and/or hydroxyalkyl groups being branched or unbranched, saturated or unsaturated.

9. Composition according to claim 8, characterized in that a is an integer between 1 and 6.

10. A composition according to claim 8 characterized in that the alkyl and/or hydroxyalkyl group(s) has/have a chain length of from 1 to 8 carbon atoms.

11. A composition according to claim 1 characterized in that the content of noionic surfactant, based on the total weight of the composition, ranges from about 1% to about 28%.

12. A composition according to claim 1 characterized in that the content of nonionic surfactant, based on the total weight of the composition, ranges from about 5% to about 25%.

13. A composition according to claim 1 characterized in that the content of noionic surfactant, based on the total weight of the composition, ranges from about 7% to about 23%.

14. A composition according to claim 1 characterized in that the noinionic surfactant is chosen from the group consisting of fatty alcohol ethoxylates, amides of alkyl fatty acids, ethoxylated fatty acid amides and polyoxyethylene polyoxypropylene block polymers.

15. Composition according to claim 14, characterized in that the nonionic surfactant is a fatty alcohol ethoxylate.

16. Composition according to claim 14, characterized in that the fatty alcohol ethoxylates have the following structure

where $R^2$ is chosen from the group consisting of branched and unbranched, saturated and unsaturated alkyl groups having from 8 to 24 carbon atoms and m is an integer between 1 and 40.

17. Composition according to claim 14, characterized in that the fatty acid amides have the following structure

and/or the ethoxylated fatty acid amides have the following structures (IIIb) and/or (IIIc)

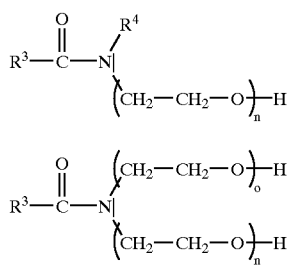

where $R^3$ is chosen from the group consisting of branched and unbranched, saturated and unsaturated alkyl groups having from 8 to 24 carbon atoms, and n and o are in each case and independently of one another an integer between 0 and 8, $R^4$ and $R^5$ are in each case and independently of one another H, an alkyl group or a hydroxyalkyl group.

18. Composition according to claim 14, characterized in that the polyoxyethylene-polyoxypropylene block polymers have from 4 to 40 ethylene oxide groups per molecule and/or from a 10 to 50 propylene oxide groups per molecule.

19. A composition according to claim 1 characterized in that the content, based on the total weight of the composition, of the ethoxylated alkyl phosphate ester component ranges from about 0.5% to about 25%.

20. A composition according to claim 19, characterized in that the content of said ethoxylated alkyl phosphate ester component ranges from about 1.5% to about 20%.

21. A composition according to claim 19, characterized in that the content of said ethoxylated alkyl phosphate ester component ranges from about 1.8% to about 18%.

22. Composition according to claim 17, characterized in that $R^4$, $R^5$ and the substituents on the N atom in $Y^1$ and $Y^2$ are in each case and independently of one another chosen from the group consisting of alkyl and/or hydroxyalkyl groups which are unbranched or branched, saturated or unstaturated and/or have a chain length of from 1 to 8 carbon atoms.

23. A composition according to claim 1, comprising at least two of said ethoxylated alkyl phosphate ester components.

24. Composition according to claim 1, characterized in that the oil component is chosen from the group consisting of natural oils having a high content of triglycerides, modified oils which comprise mixtures of mono- and diglycerides, paraffin oil, ester oils and silicone oils.

25. Composition according to claim 24, characterized in that the glycerides comprise fatty acids chosen from the group consisting of branched, unbranched, saturated and unsaturated fatty acids.

26. Composition according to claim 25, characterized in that the fatty acids have from 8 to 24 carbon atoms.

27. Composition according to claim 1, characterized in that the oil component comprising a natural oil has a high content of polyunsaturated fatty acids, the lionoleic acid to α-linolenic acid ratio being between 15:1 and 5:1.

28. Composition according to claim 27, characterized in that the ratio is between 13:1 and 7:1.

29. Composition according to claim 28, characterized in that the ratio is between 11:1 and 9:1.

30. Composition according to claim 1, characterized in that the oil component is chosen from the group consisting of paraffin oil, modified coconut oil, soybean oil, sunflower oil, wheatgerm oil, linseed oil, thistle oil and grapeseed oil.

31. Composition according to claim 30, characterized in that the modified coconut oil has a cloud point of <5° C.

32. Composition according to claim 1, characterized in that, in each case based on the total weight of the formulation the surfactant component constitutes from 15 to 35% by weight, and comprises
from 5 to 15% of TIPA laureth sulphate
from 10 to 25% of laureth-3
from 1.5 to 15% of potassium deceth-4 phosphate and
the oil component comprises
from 5 to 55% of soybean oil
from 0 to 25% of sunflower oil and
from 0 to 30% of paraffin oil.

33. A foaming oil preparation comprising the composition according to claim 1.

34. A cosmetic and/or pharmaceutical composition comprising the composition according to claim 1.

35. The composition according to claim 1 in the form of an oil bath, shower preparation, face-cleansing fluid, make-up remover or body wash.

36. A method for treating dry skin conditions and/or atopic eczema comprising applying an effective amount of the composition according to claim 1 to the affected area.

37. The method according to claim 36, characterized in that the method does not comprise additional therapy intervals.

* * * * *